US012780770B2

(12) United States Patent
Sun et al.

(10) Patent No.: US 12,780,770 B2
(45) Date of Patent: Nov. 3, 2026

(54) METHOD AND SYSTEM FOR PREPARING EPOXYPROPANE BY DIRECTLY EPOXIDIZING PROPYLENE

(71) Applicants: CHINA PETROLEUM & CHEMICAL CORPORATION, Beijing (CN); SINOPEC RESEARCH INSTITUTE OF SAFETY ENGINEERING CO., LTD., Qingdao (CN)

(72) Inventors: Bing Sun, Qingdao (CN); Chenyang Zhao, Qingdao (CN); Zhe Yang, Qingdao (CN); Hongwei Zhu, Qingdao (CN); Lin Wang, Qingdao (CN); Jie Jiang, Qingdao (CN); Ning Shi, Qingdao (CN); Na Li, Qingdao (CN); Shiqiang Wang, Qingdao (CN); Haozhi Wang, Qingdao (CN)

(73) Assignees: CHINA PETROLEUM & CHEMICAL CORPORATION, Beijing (CN); SINOPEC RESEARCH INSTITUTE OF SAFETY ENGINEERING CO., LTD., Qingdao (CN)

( * ) Notice: Subject to any disclaimer, the term of this patent is extended or adjusted under 35 U.S.C. 154(b) by 853 days.

(21) Appl. No.: 18/004,985

(22) PCT Filed: Jan. 26, 2021

(86) PCT No.: PCT/CN2021/073744

§ 371 (c)(1),
(2) Date: Jan. 10, 2023

(87) PCT Pub. No.: WO2022/007387

PCT Pub. Date: Jan. 13, 2022

(65) Prior Publication Data

US 2023/0339833 A1 Oct. 26, 2023

(30) Foreign Application Priority Data

Jul. 10, 2020 (CN) ........................ 202010662738.X
Jul. 10, 2020 (CN) ........................ 202010662744.5
Jul. 10, 2020 (CN) ........................ 202010662746.4

(51) Int. Cl.

*C07C 41/02* (2006.01)
*B01J 19/00* (2006.01)
*B01J 19/14* (2006.01)
*B01J 29/068* (2006.01)

(52) U.S. Cl.

CPC ........... *C07C 41/02* (2013.01); *B01J 19/0013* (2013.01); *B01J 19/14* (2013.01); *B01J 29/068* (2013.01)

(58) Field of Classification Search

CPC ...................................................... C07C 41/02
USPC ......................................................... 568/613
See application file for complete search history.

(56) References Cited

U.S. PATENT DOCUMENTS

2010/0197947 A1 8/2010 Narahara

FOREIGN PATENT DOCUMENTS

| | | | |
|---|---|---|---|
| CN | 1268072 | A | 9/2000 |
| CN | 107216296 | A | 9/2017 |
| CN | 108602789 | A | 9/2018 |
| CN | 110141931 | A | 8/2019 |
| CN | 111298806 | A | 6/2020 |
| JP | H10244156 | A | 9/1998 |
| JP | 2009051769 | A | 3/2009 |
| JP | 2013209391 | A | 10/2013 |
| WO | 03062196 | A2 | 7/2003 |
| WO | 2008069871 | A1 | 6/2008 |

OTHER PUBLICATIONS

CN 1268072A-machine translation.*

* cited by examiner

*Primary Examiner* — Ana Z Muresan
(74) *Attorney, Agent, or Firm* — NKL LAW; Allen Xue

(57) ABSTRACT

A method and system for preparing epoxypropane by direct epoxidation of propylene includes the steps of subjecting a mixed gas of a first feed gas and a second feed gas to a contact reaction with a catalyst under reaction conditions of propylene epoxidation to prepare epoxypropane. The first feed gas contains oxygen gas and is free or substantially free of hydrogen gas. The second feed gas contains hydrogen gas and is free or substantially free of oxygen gas. The first feed gas and/or the second feed gas contain propylene, at least one of the first feed gas and the second feed gas further contains a diluent gas. The method can be used for reducing dosage of diluent gas, preferably recycling the tail gas, thereby significantly increasing the conversion rate of propylene without compromising the service life of catalyst.

14 Claims, 1 Drawing Sheet

METHOD AND SYSTEM FOR PREPARING EPOXYPROPANE BY DIRECTLY EPOXIDIZING PROPYLENE

CROSS REFERENCE TO RELATED APPLICATIONS

This application is a U.S. national stage entry of PCT International Application No. PCT/CN2021/073744, filed on Jan. 26, 2021, which claims the priority to the Chinese Application no. 202010662746.4, filed on Jul. 10, 2020, entitled "METHOD FOR PREPARING EPOXYPROPANE BY DIRECT EPOXIDATION OF PROPYLENE", the Chinese Application No. 202010662744.5, filed on Jul. 10, 2020, entitled "METHOD AND SYSTEM FOR PREPARING EPOXYPROPANE BY DIRECT EPOXIDATION OF PROPYLENE", and the Chinese Application No. 202010662738.X, filed on Jul. 10, 2020, entitled "METHOD FOR PREPARING EPOXYPROPANE BY DIRECT EPOXIDATION OF PROPYLENE FOR THE PURPOSE OF REDUCING THE DILUENT GAS", the content of each is incorporated herein by reference in its entirety.

TECHNICAL FIELD OF THE INVENTION

The present disclosure relates to the technical field of preparing epoxypropane, and in particular to a method and system for preparing epoxypropane by direct epoxidation of propylene.

BACKGROUND ART OF THE INVENTION

Epoxypropane is a chemical having a large production and used amount worldwide, and can be used for producing the intermediate chemicals such as polyether, propylene glycol, isopropanolamine and propylene alcohol, thereby preparing unsaturated polymer resins, polyurethanes, surfactants and other chemicals. Epoxypropane is widely used in the fields of foods, textiles, medicine and chemical industry.

The methods for producing epoxypropane in the industrial field at present are mainly categorized as the chlorohydrin method, the co-oxidation method and the direct oxidation (HPPO) method. Among them, the main disadvantages of the chlorohydrin method reside in the use of toxic chlorine gas, the severe corrosion of equipment, and the generation of a large amount of chlorine-containing waste water which contaminates environment, not meeting the requirements of green chemical process and clean production, thus the process will be eventually phased out under the increasingly stringent requirements of environmental protection. Although the co-oxidation method overcomes the disadvantages of the chlorohydrin method in regard to the environmental pollution and the corrosion of equipment, it is a relatively clean production process compared to the chlorohydrin method, but the method has the disadvantages of high quality requirement of raw materials, long technological process, large investment scale, and the economic performance may be significantly influenced by the price of co-produced products.

The HPPO method is a novel process, and relates to a direct oxidation process using titanium silicalite molecular sieve as the catalyst and hydrogen peroxide as the oxidizing agent. The outstanding advantages of the reaction reside in the mild reaction conditions (room temperature ~80° C.), high selectivity, and environmentally-friendly and clean production process. However, the process also has a certain problem, such as the need for building up the hydrogen peroxide production unit.

The relevant researches have reported that $TiO_2$ supported Au nanoparticles can catalyze the reaction of oxygen gas with propylene to generate epoxypropane, the specific reaction formula is as follows:

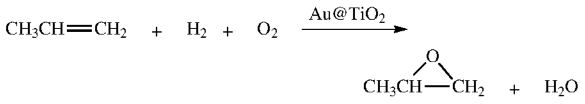

The research work has attracted widespread attentions from China and foreign countries, a great deal of researches have been carried out by the researchers to develop various metal catalysts, such as Au, Ag and Cu. The generally accepted reaction mechanism is that Au catalysts supported on $TiO_2$, TS-1 and the like initially catalyze the reaction of $H_2$ with $O_2$ to form $H_2O_2$ or —OOH species, then the intermediate species react with Ti to form Ti—OOH, which further reacts with propylene to generate epoxypropane. The process is carried out in a reactor in the presence of a catalyst and a diluent gas, for directly oxidizing propylene to prepare epoxypropane. The outstanding advantages of this reaction reside in the mild reaction conditions, high selectivity, and environmentally-friendly and clean production process. However, there are also significant defects: for example, in order to address the safety concerns, a majority of the researchers have selected to dope a large amount of inert protective gas (e.g., 70-95 vol. %) to avoid explosion of the system.

SUMMARY OF THE INVENTION

The present disclosure aims to overcome the defect in the prior art with respect to a high used amount of diluent gas during a process of preparing epoxypropane by the epoxidation of propylene, thereby provide a method and system for preparing epoxypropane by direct epoxidation of propylene. A use of the technical solution in the present disclosure can significantly reduce the used amount of a diluent gas.

In order to achieve the above object, a first aspect of the present disclosure provides a method for preparing epoxypropane by direct epoxidation of propylene comprising: subjecting a mixed gas of a first feed gas and a second feed gas to a contact reaction with a catalyst under reaction conditions of propylene epoxidation to prepare epoxypropane;

wherein the first feed gas contains oxygen gas and is free or substantially free of hydrogen gas, the second feed gas contains hydrogen gas and is free or substantially free of oxygen gas, the first feed gas and/or the second feed gas contain propylene, at least one of the first feed gas and the second feed gas further comprises a diluent gas.

Preferably, the diluent gas is an inert diluent gas and/or a non-inert diluent gas; the concentration of oxygen gas in the first feed gas and the mixed gas each independently satisfies the following formula:

$$X_{O2} \leq 1 - X_m - \frac{1}{\sum \frac{X_n}{N_n} + \frac{X_{propylene}}{N_{propylene}} + \frac{X_{hydrogen}}{N_{hydrogen}}}, \text{ or} \quad \text{Formula (1)}$$

-continued $$X_{O2} \geq 1 - X_m - \frac{1}{\sum \frac{X_n}{L_n} + \frac{X_{propylene}}{L_{propylene}} + \frac{X_{hydrogen}}{L_{hydrogen}}}; \quad \text{Formula (2)}$$

wherein, $X_{O2}$ denotes the volume fraction (%) of oxygen gas in the mixed gas;

$X_m$ denotes the volume fraction (%) of inert diluent gas m in the mixed gas;

$X_n$ denotes the volume fraction (%) of non-inert diluent gas n in the mixed gas;

$X_{propylene}$ denotes the volume fraction (%) of propylene in the mixed gas;

$X_{hydrogen}$ denotes the volume fraction (%) of hydrogen gas in the mixed gas;

$N_n$ denotes the lower explosion limit (%) of the non-inert diluent gas n in the mixed gas;

$N_{propylene}$ denotes the lower explosion limit (%) of propylene in the mixed gas;

$N_{hydrogen}$ denotes the lower explosion limit (%) of hydrogen gas in the mixed gas;

$L_n$ denotes the upper explosion limit (%) of the non-inert diluent gas n in the mixed gas;

$L_{propylene}$ denotes the upper explosion limit (%) of propylene in the mixed gas;

$L_{hydrogen}$ denotes the upper explosion limit (%) of hydrogen gas in the mixed gas.

Preferably, the diluent gas is at least one of propylene, propane, methane and ethane.

Preferably, the catalyst and inert filler are filled in the reactor in an alternately layered stacking manner.

Preferably, the propylene epoxidation is carried out with a volumetric hourly space velocity of the mixed gas of 500-30,000 mL $g_{cat}^{-1}$ $h^{-1}$.

Preferably, the method further comprises preheating the mixed gas.

In a second aspect, the present disclosure provides a reaction system for preparing epoxypropane by direct epoxidation of propylene, the reaction system comprises:

an air supply unit for supplying propylene, oxygen gas, hydrogen gas and a diluent gas;

a mixing unit comprising a first feed zone, a second feed zone and a third feed zone;

the first feed zone is used for mixing oxygen gas, optionally hydrogen gas, optionally propylene and optionally diluent gas to obtain a first feed gas;

the second feed zone is used for mixing hydrogen gas, optionally oxygen gas, optionally propylene and optionally diluent gas to obtain a second feed gas;

wherein the materials in the first feed gas and the second feed gas are selected such that the first feed gas contains oxygen gas and is free or substantially free of hydrogen gas, the second feed gas contains hydrogen gas and is free or substantially free of oxygen gas, the first feed gas and/or the second feed gas contain propylene, at least one of the first feed gas and the second feed gas further comprises a diluent gas;

the third feed zone is used for mixing the first feed gas, the second feed gas and the recycle gas to obtain a mixed gas;

a reaction unit, in which a catalyst is disposed for bringing the mixed gas into contact with the catalyst and carrying out reaction under reaction conditions of propylene epoxidation to prepare epoxypropane;

a product separation unit for separating products obtained from a propylene epoxidation to obtain the target product epoxypropane, organic by-products and a recycle gas;

a gas circulation unit, in communication with the mixing unit, for receiving the recycle gas, and conveying the recycle gas to the mixing unit as at least a portion of the reaction feed gas and the diluent gas.

Due to the aforementioned technical scheme, the present disclosure can produce the following favorable effects:

1. By mixing a first feed gas with a second feed gas to obtain a mixed gas, wherein the first feed gas contains oxygen gas and is free or substantially free of hydrogen gas, the second feed gas contains hydrogen gas and is free or substantially free of oxygen gas, the first feed gas and/or the second feed gas contain propylene, at least one of the first feed gas and the second feed gas further comprises a diluent gas, the present disclosure can avoid a circumstance that the hydrogen gas concentration is rapidly reduced to be within the explosion limit of the mixed combustible gas system during the mixing process of hydrogen gas and oxygen gas; as can be seen, the method of the present disclosure fulfills the purpose that the reaction feed gases are blended in a more homogenous manner and the burning and explosion risk is further reduced.
2. The technical solution of the disclosure can reduce the used amount of the diluents gas, and further increase concentration of reactant gases under a premise of lowering the separation pressure of subsequent products, thereby improving the reaction selectivity and conversion rate and reducing the energy consumption.
3. The technical solution of the present disclosure enables more effective mixing of the reactant gases, reducing the influence on the catalyst when the reactant gases are in contact with the catalyst, thereby significantly extending the service life of the catalyst, the service life of the catalyst in tubular reactors may extend from the conventional 100 hours to more than 500 hours.
4. In a preferred embodiment, the present disclosure uses a gaseous phase circulation process for carrying out a targeted treatment on the unreacted feed gas and recycling the unreacted feed gas to the reactor, so as to further carry out reaction, the utilization ratio of raw materials is significantly improved, and the comprehensive conversion rate of the propylene is significantly increased under a premise of ensuring the space-time yield of epoxypropane. In addition, the reaction tail gas is recycled under a premise of ensuring the reaction safety, such that the production costs and the pressure of tail gas treatment are alleviated.
5. In a preferred embodiment, the technical solution of the present disclosure can efficiently utilize the reactant gases without affecting the service life of said catalyst.

DESCRIPTION OF REFERENCE SIGNS

Figure 1:
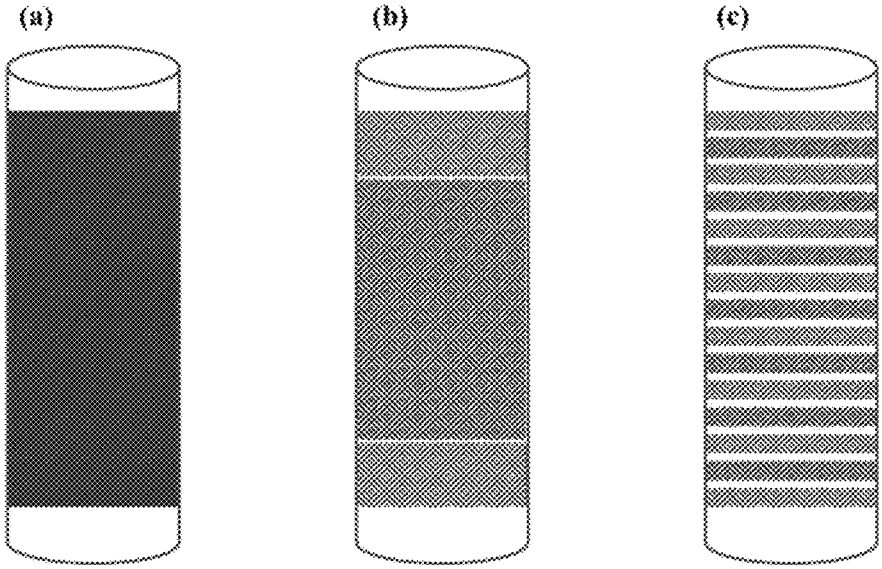
FIGS. 1A to 1C illustrate a filling mode of the catalyst provided by the present disclosure.

1. Air supply unit
2. Mixing unit

3. Reaction unit
4. Product separation unit
5. Gas circulation unit
6. Analysis unit

DETAILED DESCRIPTION OF THE INVENTION

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

In a first aspect, the present disclosure provides a method for preparing epoxypropane by direct epoxidation of propylene comprising: subjecting a mixed gas of a first feed gas and a second feed gas to a contact reaction with a catalyst under reaction conditions of propylene epoxidation to prepare epoxypropane;

wherein the first feed gas contains oxygen gas and is free or substantially free of hydrogen gas, the second feed gas contains hydrogen gas and is free or substantially free of oxygen gas, the first feed gas and/or the second feed gas contain propylene, at least one of the first feed gas and the second feed gas further comprises a diluent gas.

According to the present disclosure, the diluent gas may be any diluent gas that can be used for the direct epoxidation of propylene, such as an inert gas or a non-inert gas, or a mixed diluent gas of an inert gas and a non-inert gas. Therefore, the diluent gas is an inert diluent gas and/or a non-inert diluent gas.

According to the present disclosure, the inert diluent gas may be selected from the group consisting of $N_2$, Ar and $CO_2$.

According to the present disclosure, the non-inert gas is preferably a gaseous alkane and/or a gaseous alkene.

Preferably, the gaseous alkane is a $C_1$-$C_4$ alkane, and according to another particularly preferred embodiment of the present disclosure, the gaseous alkane is methane, ethane and propane, more preferably propane.

Preferably, the gaseous alkene is a $C_2$-$C_4$ olefin, and according to an especially preferred embodiment of the present disclosure, the gaseous alkene is propylene.

According to the present disclosure, the proportion of the diluent gas in the first feed gas or the second feed gas is not particularly limited, it may be any value or range within 0-100% of the total diluent gas, for instance, 0, 0.01%, 0.1%, 1%, 10%, 20%, 30%, 40%, 50%, 60%, 70%, 80%, 90%, 100%, 0.05-100%, 50-90% and the likes According to the present disclosure, the proportion of propylene in the first feed gas or the second feed gas is not particularly limited, it may be any value or range within 0-100% of total propylene, for instance, 0, 0.01%, 0.1%, 1%, 10%, 20%, 30%, 40%, 50%, 60%, 70%, 80%, 90%, 100%, 0.05-100%, 50-90% and the likes According to the present disclosure, "substantially free of hydrogen gas" refers to that the amount of hydrogen gas contained in the first feed gas is insufficient to trigger an explosion, e.g., the volume fraction of hydrogen gas in the first feed gas is less than 4% (excluding 4%), for example, 3.5% or less, 3% or less, 2.5% or less, 2% or less, 1.5% or less, 1% or less, 0.5% or less, 0.1% or less.

Wherein the expression "substantially free of oxygen gas" means that the amount of oxygen gas contained in the second feed gas is insufficient to trigger an explosion, e.g., the volume fraction of oxygen gas in the second feed gas is less than 25% (excluding 25%), e.g., 20% or less, 15% or less, 10%, 8% or less, 5% or less, 4% or less, 3% or less, 2% or less, 1% or less, 0.5% or less, 0.1% or less.

In accordance with a preferred embodiment of the present disclosure, the first feed gas contains oxygen gas and is free or substantially free of hydrogen gas, contains at least a portion of propylene and at least a portion of a diluent gas; the second feed gas contains hydrogen gas and is free or substantially free of oxygen gas, contains the remainder of propylene and the remainder of the diluent gas; or The second feed gas contains hydrogen gas and is free or substantially free of oxygen gas, contains at least a portion of propylene and at least a portion of a diluent gas; the first feed gas contains oxygen gas and is free or substantially free of hydrogen gas, contains the remainder of propylene and the remainder of the diluent gas.

According to a further preferred embodiment A of the present disclosure, the first feed gas contains oxygen gas and is free or substantially free of hydrogen gas, contains all the propylene and all the diluent gas; the second feed gas contains hydrogen gas and is free or substantially free of oxygen gas.

According to a further preferred embodiment B of the present disclosure, the first feed gas contains oxygen gas and is free or substantially free of hydrogen gas, contains all the propylene and a portion of diluent gas (>0); the second feed gas contains hydrogen gas and is free or substantially free of oxygen gas, contains the remainder of the diluent gas.

According to a further preferred embodiment C of the present disclosure, the first feed gas contains oxygen gas and is free or substantially free of hydrogen gas, contains a portion of propylene (>0) and a portion of diluent gas (>0); the second feed gas contains hydrogen gas and is free or substantially free of oxygen gas, contains the remainder of propylene and the remainder of the diluent gas.

According to a further preferred embodiment D of the present disclosure, the first feed gas contains oxygen gas and is free or substantially free of hydrogen gas, contains a portion of propylene (>0) and all the diluent gas; the second feed gas contains hydrogen gas and is free or substantially free of oxygen gas, contains the remainder of propylene.

According to a further preferred embodiment E of the present disclosure, the first feed gas contains oxygen gas and is free or substantially free of hydrogen gas, contains all the diluent gas; the second feed gas contains hydrogen gas and is free or substantially free of oxygen gas, contains all the propylene.

According to a further preferred embodiment F of the present disclosure, the first feed gas contains oxygen gas and is free or substantially free of hydrogen gas, contains a portion of diluent gas (>0); the second feed gas contains hydrogen gas and is free or substantially free of oxygen gas, contains the remainder of the diluent gas and all the propylene.

According to a further preferred embodiment G of the present disclosure, the first feed gas contains oxygen gas and is free or substantially free of hydrogen gas, contains a portion of propylene (>0); the second feed gas contains hydrogen gas and is free or substantially free of oxygen gas, contains all the diluent gas and the remainder of propylene.

According to a further preferred embodiment H of the present disclosure, the first feed gas contains oxygen gas and is free or substantially free of hydrogen gas; the second feed gas contains hydrogen gas and is free or substantially free of oxygen gas, contains all the propylene and all the diluent gas.

In the present disclosure, as described above, "a portion of diluent gas" as mentioned above refers to any numerical number between 0-100 vol % (excluding endpoint values), e.g., 0.1 vol %, 1 vol %, 5 vol %, 10 vol %, 15 vol %, 20 vol %, 25 vol %, 30 vol %, 35 vol %, 40 vol %, 45 vol %, 50 vol %, 55 vol %, 60 vol %, 65 vol %, 70 vol %, 75 vol %, 80 vol %, 85 vol %, 90 vol %, 91 vol %, 92 vol %, 93 vol %, 94 vol %, 95 vol %, 96 vol %, 97 vol %, 98 vol %, 99 vol %, 99.5 vol %.

In the present disclosure, as described above, "a portion of propylene" as mentioned above refers to any numerical number between 0-100 vol % (excluding endpoint values), e.g., 0.1 vol %, 1 vol %, 5 vol %, 10 vol %, 15 vol %, 20 vol %, 25 vol %, 30 vol %, 35 vol %, 40 vol %, 45 vol %, 50 vol %, 55 vol %, 60 vol %, 65 vol %, 70 vol %, 75 vol %, 80 vol %, 85 vol %, 90 vol %, 91 vol %, 92 vol %, 93 vol %, 94 vol %, 95 vol %, 96 vol %, 97 vol %, 98 vol %, 99 vol %, 99.5 vol %.

According to a preferred embodiment of the present disclosure, the concentration of oxygen gas in the first feed gas and the mixed gas each independently satisfies the following formula:

$$X_{O2} \leq 1 - X_m - \frac{1}{\sum \frac{X_n}{N_n} + \frac{X_{propylene}}{N_{propylene}} + \frac{X_{hydrogen}}{N_{hydrogen}}}, \text{ or} \qquad \text{Formula (1)}$$

$$X_{O2} \geq 1 - X_m - \frac{1}{\sum \frac{X_n}{L_n} + \frac{X_{propylene}}{L_{propylene}} + \frac{X_{hydrogen}}{L_{hydrogen}}}, \qquad \text{Formula (2)}$$

wherein, $X_{O2}$ denotes the volume fraction (%) of oxygen gas in the mixed gas;

$X_m$ denotes the volume fraction (%) of inert diluent gas m in the mixed gas;

$X_n$ denotes the volume fraction (%) of non-inert diluent gas n in the mixed gas;

$X_{propylene}$ denotes the volume fraction (%) of propylene in the mixed gas;

$X_{hydrogen}$ denotes the volume fraction (%) of hydrogen gas in the mixed gas;

$N_n$ denotes the lower explosion limit (%) of the non-inert diluent gas n in the mixed gas;

$N_{propylene}$ denotes the lower explosion limit (%) of propylene in the mixed gas;

$N_{hydrogen}$ denotes the lower explosion limit (%) of hydrogen gas in the mixed gas;

$L_n$ denotes the upper explosion limit (%) of the non-inert diluent gas n in the mixed gas;

$L_{propylene}$ denotes the upper explosion limit (%) of propylene in the mixed gas;

$L_{hydrogen}$ denotes the upper explosion limit (%) of hydrogen gas in the mixed gas.

In the above preferred embodiment, an explosion of the reaction system can be effectively avoided by controlling the concentration of oxygen gas to be within the range of Formula (1) or Formula (2) mentioned above, such that the reaction can be carried out safely.

It should be noted, when the concentration of oxygen gas in the first feed gas is controlled, the mixed gas as mentioned above refers to the first feed gas, and when the concentration of oxygen gas in the mixed gas is controlled, the mixed gas as mentioned above refers to a gas mixture.

It is understandable that when the diluent gas is only an inert diluent gas, the addition sum of a non-inert diluent gas in the formula is zero; when the diluent gas is only a non-inert diluent gas, the parameter $X_m$ in the formula is zero; when the diluent gas is a mixture of an inert gas and a non-inert gas, the formulas are calculated according to respective proportion of the inert gas and the non-inert gas.

According to the present disclosure, the explosion limit range of propylene is defined as the explosion limit range determined by the combustion and explosion test method for combustible gas in an enclosed space under the room temperature and atmospheric pressure (the test is performed according to the relevant provisions in the National Standard GB/T12474-2008 of China). The explosion limit range is 2-11%, wherein the lower explosion limit is 2% and the upper explosion limit is 11%.

It is understandable that when propylene is used as a diluents gas, $X_{propylene}$ may refer to the volume fraction of total propylene in the system, the addition sum of propylene as a diluent gas is zero; in addition, the formula may be calculated based on the amount of propylene used as a diluent gas and the amount of propylene used as a reactant gas.

According to the present disclosure, the explosion limit range of hydrogen gas is defined as the explosion limit range determined by the combustion and explosion test method for combustible gas in an enclosed space under the room temperature and atmospheric pressure (the test is performed according to the relevant provisions in the National Standard GB/T12474-2008 of China). The explosion limit range is 4-75%, wherein the lower explosion limit is 4% and the upper explosion limit is 75%.

According to the present disclosure, the explosion limit range of methane is defined as the explosion limit range determined by the combustion and explosion test method for combustible gas in an enclosed space under the room temperature and atmospheric pressure (the test is performed according to the relevant provisions in the National Standard GB/T12474-2008 of China). The explosion limit range is 5-15%, wherein the lower explosion limit is 5% and the upper explosion limit is 15%.

According to the present disclosure, the explosion limit range of ethane is defined as the explosion limit range determined by the combustion and explosion test method for combustible gas in an enclosed space under the room temperature and atmospheric pressure (the test is performed according to the relevant provisions in the National Standard GB/T12474-2008 of China). The explosion limit range is 3-16%, wherein the lower explosion limit is 3% and the upper explosion limit is 16%.

According to the present disclosure, the explosion limit range of propane is defined as the explosion limit range determined by the combustion and explosion test method for combustible gas in an enclosed space under the room temperature and atmospheric pressure (the test is performed according to the relevant provisions in the National Standard GB/T12474-2008 of China). The explosion limit range is 2-10%, wherein the lower explosion limit is 2% and the upper explosion limit is 10%.

The inventors of the present disclosure have innovatively found that, in the case of using propylene as a diluent gas, propylene acts as both a diluent gas and a reactant gas, can further promotes the forward direction proceeding of the reaction. In the case of using propane as a diluent gas, the propane can effectively suppress the occurrence of side reactions, thereby improving the selectivity of epoxypropane. It shall be explained in the disclosure that the term "in the case of using propane as a diluent gas" refers to that at least a portion of the diluent gas is replaced by propylene, thereby causing a significantly excessive amount of propylene in the reaction feed gas, the excessive degree is more than the level in the general condition for promoting the forward direction proceeding of the reaction by increasing the dosage of reaction feedstock, therefore, in this case, it cannot be simply considered that the propylene is excessive, unlike the excessive amount in the conventional understanding of meanings.

According to the present disclosure, in order to further facilitate the industrial production and improve the effect of the present disclosure, it is preferable that the concentration of oxygen gas in the mixed gas satisfies the formula (1).

According to the present disclosure, it can be determined from the above content that the first feed gas may be pure oxygen gas, or a mixed gas of oxygen gas and diluent gas; in the latter case of the first feed gas, the concentration of oxygen gas is not particularly limited in the disclosure.

According to the present disclosure, when the first feed gas contains oxygen gas, diluent gas, propylene and optionally hydrogen gas, the concentration of oxygen gas preferably satisfies the formulation (1), and the concentration of oxygen gas in the first feed gas is preferably not higher than 82 vol %, for example, 15 vol %, 20 vol %, 25 vol %, 30 vol %, 35 vol %, 40 vol %, 45 vol %, 50 vol %, 55 vol %, 60 vol %, 69 vol %, 76 vol %, 79 vol % or less, in the preferred circumstance, the first feed gas may be controlled in a safety range.

According to the present disclosure, the concentration of the diluent gas in the mixed gas can be reduced to 70 vol % or less, for example, 65 vol %, 60 vol %, 55 vol %, 50 vol %, 45 vol %, 40 vol %, 35 vol %. In accordance with the technical solution and method in the prior art, the concentration of the diluent gas is generally 70 vol % or more. As can be seen, the method of the present disclosure can effectively reduce concentration of the diluent gas, thereby further increasing the concentration of the reactant gas and improving the reaction efficiency.

According to the present disclosure, the concentration of oxygen gas in the mixed gas preferably satisfies the formula (1) under the technical solution of the present disclosure, and the concentration of oxygen gas in the mixed gas can be increased to 5 vol %, preferably 10 vol % or more, not more than 60 vol %, for example, 11 vol %, 12 vol %, 13 vol %, 14 vol %, 15 vol %, 16 vol %, 17 vol %, 18 vol %, 19 vol %, 20 vol %, 21 vol %, 22 vol %, 23 vol %, 24 vol %, 25 vol %, 26 vol %, 27 vol %, 28 vol %, 29 vol %, 30 vol %, 32 vol %, 34 vol %, 36 vol %, 38 vol %, 40 vol %, 42 vol %, 44 vol %, 46 vol %, 48 vol %, 50 vol %, 52 vol %, 54 vol %, 56 vol %, 58 vol %, 60 vol %. In contrast, the concentration of oxygen gas is generally below 10 vol %, more preferably below 5 vol % according to the technical solution and method in the prior art. As can be seen, the method of the present disclosure can effectively increase the concentration of oxygen gas.

According to the present disclosure, the second feed gas is designed to mix with the first feed gas in a counter-flushing manner so as to obtain a more sufficient mixing. This may be achieved by arranging the delivery pipeline of the second feed gas and the delivery pipeline of the first feed gas. It shall be noted that the counter-flushing is defined as the mixing of two air streams in a collision form, the collision may be that the two air streams collide at an angle of 90-270° (e.g. 180°), wherein the spraying of the two air streams in the same direction is defined as 0° and the spraying of the two air streams in opposite directions is defined as 180°.

According to the present disclosure, in order to further increase efficiency of the reaction, the mixed gas is preferably subjected to preheating prior to contacting the mixed gas with the catalyst.

According to the present disclosure, the degree of preheating is preferably at least 50%, for example, 50%, 55%, 60%, 65%, 70%, 75%, 80%, 85%, preferably more than 80%, of the target reaction temperature.

According to the present disclosure, the propylene epoxidation may be carried out in a conventional reactor in the art, for example, various tubular reactors which are conventional in the art, such as reactors made of stainless steel, resin, quartz, organic glass and ceramic glass. As another example, the reactors may be various microchannel reactors which are conventional in the art.

According to the present disclosure, the catalyst may have any size and shape suitable for the tubular reactor or the microchannel reactor.

According to the present disclosure, the catalyst may be any catalyst disclosed in the prior art which is capable of catalytically reacting with propylene, oxygen gas, hydrogen gas and diluent gas to produce epoxypropane. Preferably, the catalyst is a supported metal catalyst comprising a carrier and an active metal component, wherein the active metal component may be at least one selected from the group consisting of gold, silver, copper, ruthenium, palladium, platinum, rhodium, cobalt, nickel, tungsten, bismuth, molybdenum and oxides thereof, preferably gold. The carrier for supporting the metal may be carbon black, activated carbon, silica, alumina, ceria and zeolite, preferably zeolite, more preferably a titanium-silicon molecular sieve.

According to the present disclosure, the content of the metal in terms of the metal element in the supported metal catalyst may vary within a wide range, for example, the content of the active metal component in terms of the metal element in the catalyst may be 0.01-50 wt %, for example, the content may be 0.01 wt %, 0.05 wt %, 0.06 wt %, 0.07 wt %, 0.08 wt %, 0.09 wt %, 0.1 wt %, 0.2 wt %, 0.3 wt %, 0.4 wt %, 0.5 wt %, 0.6 wt %, 0.7 wt %, 0.8 wt %, 0.9 wt %, 1 wt %, 1.1 wt %, 1.2 wt %, 1.3 wt %, 1.4 wt % 1.5 wt %, 1.6 wt %, 1.7 wt %, 1.8 wt %, 1.9 wt %, 2 wt %, 3 wt %, 4 wt %, 5 wt %, 10 wt %, 15 wt %, 20 wt %, 25 wt %, 30 wt %, 35 wt %, 40 wt %, 45 wt %, 50 wt %, preferably 0.05-5 wt %, more preferably 0.1-2 wt %, based on the total weight of the catalyst.

According to a preferred embodiment of the present disclosure, the catalyst is a gold-loaded titanium-silicon molecular sieve (Au@TS-1), wherein the loading amount of the active metal component in terms of the element Au is within a range of 0.1-2 wt %. Wherein the TS-1 molecular sieve may be prepared by means of hydrothermal synthesis, and the active metal component Au may be loaded by means of the deposition-precipitation process.

According to the present disclosure, the catalyst may be filled alone in a reactor for propylene epoxidation (as shown in FIG. 1A) or in combination with other inert materials. However, in order to further increase the service life of the catalyst, increase the reaction selectivity, the conversion rate, the space-time yield and the hydrogen gas utilization rate, and reduce the used amount of the catalyst, it is preferable that the catalyst is filled in the reactor in a form of combining the catalyst with an inert filler, wherein the inert filler may be an inert solid phase substance conventionally used in the art, and preferably the inert filler is at least one selected from the group consisting of silica sand, $Al_2O_3$, porous silica gel and ceramic ring.

Wherein the used amount of the inert filler may vary within a wide range, but preferably, the used amount of the inert filler is 1-200 parts by weight (for example, 1 part by weight, 10 parts by weight, 15 parts by weight, 20 parts by weight, 25 parts by weight, 30 parts by weight, 35 parts by weight, 40 parts by weight, 45 parts by weight, 50 parts by weight, 80 parts by weight, 90 parts by weight, 95 parts by weight, 100 parts by weight, 105 parts by weight, 110 parts by weight, 115 parts by weight, 120 parts by weight, 125 parts by weight, 130 parts by weight, 135 parts by weight, 140 parts by weight, 145 parts by weight, 150 parts by weight, 160 parts by weight, 170 parts by weight, 180 parts by weight, 190 parts by weight, 200 parts by weight), preferably 15-50 parts by weight, and more preferably 30-45 parts by weight, relative to 1 part by weight of the catalyst.

The mode of combining the catalyst and the inert filler are not particularly limited in the present disclosure, for example, the catalyst and the inert filler can be directly mixed and then filled in the reactor, or the catalyst and the inert filler can be designed with a sandwich structure (as shown in FIG. 1B), wherein the catalyst or the inert filler is disposed in the middle. However, the present inventors have found in the researches that the catalyst and the inert filler are preferably filled in the reactor in a layered stacking manner, more preferably, the catalyst and the inert filler are filled in the reactor in an alternately layered stacking manner (as shown in FIG. 1C), that can further increase service life of the catalyst, the selectivity, conversion rate, space-time yield of the reaction, and the hydrogen gas utilization rate, and reduce the used amount of the catalyst. Wherein under the stacking manner, the height of each layer of the catalyst and the height of each layer of the inert filler can be selected from a wide range, the catalyst and the inert filler are subjected to the layered stacking by means of an equal height fashion or an unequal height fashion; and preferably, each layer of the catalyst and each layer of the inert filler are independently subjected to stacking in a mode of 1-2,000 layers/m, for example, 1 layer/m, 2 layers/m, 3 layers/m, 4 layers/m, 5 layers/m, 6 layers/m, 7 layers/m, 8 layers/m, 9 layers/m, 10 layers/m, 15 layers/m, 18 layers/m, 20 layers/m, 50 layers/m, 100 layers/m, 200 layers/m, 300 layers/m, 400 layers/m, 500 layers/m, 600 layers/m, 700 layers/m, 800 layers/m, 900 layers/m, 1,000 layers/m, 1,200 layers/m, 1,400 layers/m, 1,600 layers/m, 1,800 layers/m, 2,000 layers/m, preferably 1,000-2,000 layers/m, or 10-20 layers/m.

According to the present disclosure, the layer height ratio of each layer of the catalyst and each layer of the inert filler may vary within a wide range, and preferably, in order to further enhance the effect of the present disclosure, the layer height ratio of each layer of the catalyst and each layer of the inert filler is 1:1-10, for example, the layer height ratio may be 1:1, 1:2, 1:3, 1:4, 1:5, 1:6, 1:7, 1:8, 1:9, 1:10, preferably 1:1-3, and further preferably 1:1.5-2.5.

According to the present disclosure, the manner of filling the catalyst in the reactor may be not particularly restricted, for example, a coating method, an electrodeposition method, a solution electroplating method, a mechanical filling method may be employed.

According to the present disclosure, it is preferred that the filling amount of the catalyst is 10-50 g with respect to a reactor having a volume of 1,000 mL. Under normal conditions, the filling amount of the catalyst is at least 100 g, as can be seen, the technical solution of the present disclosure can further reduce the loading amount of the catalyst.

According to the present disclosure, the temperature of the propylene epoxidation may be a conventional reaction temperature in the art, for example, 20-300° C., however, in order to further increase the conversion rate, selectivity, space-time yield of the reaction and the utilization rate of hydrogen gas, and extend the service life of the catalyst, and reduce the used amount of the catalyst, the reaction temperature is preferably 50-250° C., more preferably 120-200° C., for example, 120° C., 125° C., 130° C., 135° C., 140° C., 145° C. 150° C., 155° C., 160° C., 165° C., 170° C., 175° C., 180° C., 185° C., 190° C., 195° C., 200° C.

The inventors of the present disclosure have discovered in researches that the temperature rise rate of the system can also further influence the conversion rate, selectivity, space-time yield of the reaction and the utilization rate of hydrogen gas, the service life of the catalyst, the used amount of the catalyst; when the temperature of the reaction system is raised to the temperature required for the propylene epoxidation through an intermittent temperature rise manner, it can further increase the conversion rate, selectivity, space-time yield of the reaction and the utilization rate of hydrogen gas, extend the service life of the catalyst, reduce the used amount of the catalyst and the diluent gas. Preferably, the intermittent temperature rise mode comprises: maintaining the temperature at the raised temperature for 5-10 minutes (e.g., 5 min, 6 min, 7 min, 8 min, 9 min, 10 min) after each temperature rise of 5-10° C. (e.g., 5° C., 6° C., 7° C., 8° C., 9° C., 10° C.).

More preferably, when the temperature of the reaction system is raised to the temperature required for the propylene epoxidation at a temperature rise rate of 0.1-10° C. $min^{-1}$, preferably 0.5-5° C. $min^{-1}$, more preferably 0.5-2° C. $min^{-1}$ (the temperature rise rate may be, for example, 0.5° C. $min^{-1}$, 0.8° C. $min^{-1}$, 1.0° C. $min^{-1}$, 1.2° C. $min^{-1}$, 1.5° C. $min^{-1}$, 2.0° C. $min^{-1}$, more preferably 0.8-1.5° C. $min^{-1}$), it is possible to still further increase the conversion rate, selectivity, space-time yield of the reaction and the utilization rate of hydrogen gas, extend the service life of said catalyst, reduce the used amount of the catalyst and the diluent gas.

According to the present disclosure, the pressure of the propylene epoxidation may be a conventional reaction pressure in the art, for example, the pressure may be 0-5 MPa; however, in order to further increase the conversion rate, selectivity, space-time yield of the reaction and the utilization rate of hydrogen gas, extend the service life of the catalyst, reduce the used amount of the catalyst, the reaction pressure is preferably 0-1.5 MPa, more preferably 0.05-0.25 MPa; for example, the reaction pressure may be 0.05 MPa, 0.06 MPa, 0.07 MPa, 0.08 MPa, 0.09 MPa, 0.1 MPa, 0.11 MPa, 0.12 MPa, 0.13 MPa, 0.14 MPa, 0.15 MPa, 0.17 MPa, 0.19 MPa, 0.21 MPa, 0.23 MPa, 0.25 MPa.

According to the present disclosure, the hourly space velocity of the propylene epoxidation may be a conventional volumetric hourly space velocity of reaction in the art; however, in order to further increase the conversion rate, selectivity, space-time yield of the reaction and the utilization rate of hydrogen gas, extend the service life of the catalyst, reduce the used amount of the catalyst, the volumetric hourly space velocity of the mixed gas is preferably 500-30,000 ml $g_{cat}^{-1}$ $h^{-1}$, more preferably 1,000-20,000 mL $g_{cat}^{-1}$ $h^{-1}$, further preferably 2,000-15,000 mL $g_{cat}^{-1}$ $h^{-1}$, and for example, the volumetric hourly space velocity may be 2,000 mL $g_{cat}^{-1}$ $h^{-1}$, 3,000 mL $g_{cat}^{-1}$ $h^{-1}$, 4,000 mL $g_{cat}^{-1}$ $h^{-1}$, 5,000 mL $g_{cat}^{-1}$ $h^{-1}$, 6,000 mL $g_{cat}^{-1}$ $h^{-1}$, 7,000 mL $g_{cat}^{-1}$ $h^{-1}$ 8,000 mL $g_{cat}^{-1}$ $h^{-1}$, 9,000 mL $g_{cat}^{-1}$ $h^{-1}$, 10,000 mL $g_{cat}^{-1}$ $h^{-1}$, 12,000 mL $g_{cat}^{-1}$ $h^{-1}$, 13,000 mL $g_{cat}^{-1}$ $h^{-1}$, 14,000 mL $g_{cat}^{-1}$ $h^{-1}$, 15,000 mL $g_{cat}^{-1}$ $h^{-1}$.

According to the present disclosure, the propylene epoxidation provided by the method of the present application is preferably performed in the absence of a solvent, wherein the solvent comprises any exogenously introduced liquid phase.

According to a preferred embodiment of the present disclosure, the method further comprises: separating the reaction products to obtain the target product epoxypropane, an organic by-product and a tail gas, and the tail gas is then subjected to post-treatment and mixing into the mixed gas as at least a portion of the reaction feed gas with a diluent gas for recycling. Due to the recycling, the utilization rate of the raw materials is greatly increased, and the comprehensive conversion rate of propylene is significantly increased under the premise of ensuring the space-time yield of the epoxypropane.

Preferably, the post-treatment comprises washing, optional condensation, optional ingredient adjustment and pressurization in sequence.

Preferably, the washing is an alcohol washing. The alcohol may be one or more selected from the group consisting of methanol, ethanol, propanol, n-butanol, isobutanol and ethylene glycol.

According to a preferred embodiment of the disclosure, the tail gas is subjected to a low temperature washing with an alcohol, more preferably, the reacted gas is subjected to a multi-stage low temperature alcohol washing, e.g. 2-3 stages. The low temperature may be 2-20° C.

According to a preferred embodiment of the present disclosure, the post-treatment comprises:

1) Washing the tail gas and analyzing the composition of the obtained washing process gas, and mixing the washing process gas as a recycle gas into the mixed gas for recycling if the composition of the washing process gas is within a predetermined range, and condensing the washing process gas if the composition of the washing process gas is not within a predetermined range.
2) Subjecting the washing process gas to at least one stage of condensation to obtain a condensate and a non-condensable process gas, subjecting the non-condensable process gas to a composition analysis, and mixing the non-condensable process gas as a recycle gas into the mixed gas for recycling if the composition of the non-condensable process gas is within a predetermined range, or performing the gas conditioning treatment if the composition of the non-condensable process gas is not within a predetermined range.
3) Adjusting the composition of the non-condensable process gas by introducing at least one of propylene, hydrogen gas, oxygen gas and a diluent gas, and analyzing the composition of the obtained adjustment process gas, and mixing the adjustment process gas as a recycle gas into the mixed gas for recycling if the composition of the adjustment process gas is within a predetermined range, or discharging the adjustment process gas if the composition of the adjustment process gas is not within a predetermined range.

Wherein the composition analysis may be accomplished by using a gas chromatograph. For example, the gas to be analyzed is introduced into a gas chromatograph equipped with a thermal conductivity detector (TCD) and a flame ionization detector (FID) for subjecting to an analysis.

Preferably, the concentrations of ingredients in the gas are obtained after the composition analysis, and the concentrations of the ingredients in the gas are adjusted to the predetermined concentrations according to the reaction requirements through a mass flow meter, the gas is then used for recycling.

In step (b), the tail gas from alcohol washing may be condensed by a low temperature condensing collector (i.e., cold trap), the ingredients of the tail gas from alcohol washing can be separately condensed according to the boiling points thereof to form a condensate, the condensate is then subjected to a cyclone separation by a low temperature circulation refrigeration pump.

According to the present disclosure, "the composition is within a predetermined range" refer to that the contents of the ingredients of the corresponding gas is stable and within a safe range without exceeding the limiting oxygen gas content.

More preferably, in order to ensure the accuracy of the analysis, each process gas to be subjected to the component analysis is transported into the gas chromatograph under the heating condition of 50-200° C., in particular, a heating belt may be arranged to maintain a temperature of 50-200° C., preferably 80-150° C., for example, 80° C., 90° C., 100° C., 110° C., 120° C., 130° C., 140° C., 150° C.

Figure 2:
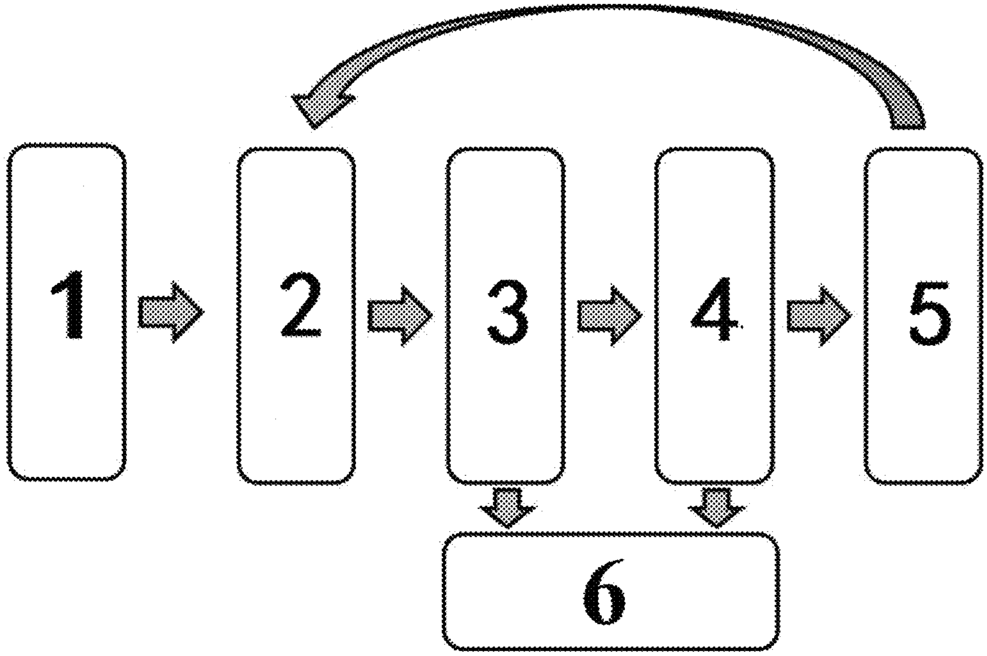
FIG. 2 illustrates a schematic diagram of the system for preparing epoxypropane by direct epoxidation of propylene provided by the present disclosure.

In a second aspect, as shown in FIG. 2, the present disclosure provides a reaction system for preparing epoxypropane by direct epoxidation of propylene, the reaction system comprises:

- an air supply unit 1 for supplying propylene, oxygen gas, hydrogen gas and a diluent gas;
- a mixing unit 2 comprising a first feed zone, a second feed zone and a third feed zone;
- the first feed zone is used for mixing oxygen gas, optionally hydrogen gas, optionally propylene and optionally diluent gas to obtain a first feed gas;
- the second feed zone is used for mixing hydrogen gas, optionally oxygen gas, optionally propylene and optionally diluent gas to obtain a second feed gas;
- wherein the materials in the first feed gas and the second feed gas are selected such that the first feed gas contains oxygen gas and is free or substantially free of hydrogen gas, the second feed gas contains hydrogen gas and is free or substantially free of oxygen gas, the first feed gas and/or the second feed gas contain propylene, at least one of the first feed gas and the second feed gas further comprises a diluent gas;
- the third feed zone is used for mixing the first feed gas, the second feed gas and the recycle gas to obtain a mixed gas;
- a reaction unit 3, in which a catalyst is disposed for bringing the mixed gas into contact with the catalyst and carrying out reaction under reaction conditions of propylene epoxidation to prepare epoxypropane;
- a product separation unit 4 for separating products obtained from a propylene epoxidation to obtain the target product epoxypropane, organic by-products and a recycle gas;
- a gas circulation unit 5, in communication with the mixing unit, for receiving the recycle gas, and conveying the recycle gas to the mixing unit as at least a portion of the reaction feed gas and the diluent gas.

Preferably, in the third feed zone, a pipeline for introducing the first feed gas and a pipeline for introducing the second feed gas are arranged such that the first feed gas is mixed with the second feed gas in a counter-flushing manner. It should be noted that the counter-flushing herein refers to the mixing of two air streams in a collision form, the collision may be that the two air streams collide at an angle of 90-270° (e.g. 180°), wherein the spraying of the two air streams in the same direction is defined as 0° and the spraying of the two air streams in opposite directions is defined as 180°.

In order to further improve the effects of the present disclosure, the mixing unit further comprises a gas preheating zone arranged downstream the third feed zone, wherein a preheating device is arranged in the gas preheating zone and may be designed with the same structure of the reactor, or different structure with the reactor. The device is further provided with heating elements and temperature control elements to heat the reaction feed gas to a predetermined temperature.

According to a preferred embodiment of the present disclosure, the preheating device is designed with a coiled tube type, and can heat the reaction feed gas by means of heat-conducting oil, molten salt, electric heating and the like.

According to a preferred embodiment of the present disclosure, in order to increase the propylene conversion rate, the product separation unit comprises a product separation zone, a gas washing zone, a gas condensing zone and a gas conditioning zone sequentially connected in series, and the product separation zone, the gas washing zone, the gas condensing zone and the gas conditioning zone are each independently in communication with the gas circulation unit.

According to the present disclosure, in order to better control the pressure and flow rate of the reaction product gas obtained after the reaction, it is preferable to further provide a regulating valve, for example, a back pressure valve, at the outlet of the reaction unit to adjust the pressure and flow rate of the reaction product gas.

According to the present disclosure, it is preferred that the reaction system further comprises an analysis unit 6 for performing a composition analysis on the process gas requiring a composition analysis.

According to the present disclosure, it is preferred that the reaction unit is further in communication with the analysis unit, whereby the reaction product may be divided into at least two branches, wherein one branch is used for feeding a portion of the reaction product to the analysis unit, and the other branch is used for transporting the remaining reaction product to the product separation unit for carrying out the post-treatment.

According to the present disclosure, it is preferred that the product separation zone is adapted to separate products obtained from a propylene epoxidation, in order to obtain the target product epoxypropane, an organic by-product and a tail gas (comprising a diluent gas and insufficiently reacted feed gas), the tail gas is transported by a branch to the analysis unit for subjecting to a total component analysis, and the remaining tail gas is transported by another branch to the gas washing zone for washing the tail gas to obtain a washing process gas. Thus, it is preferred that the product separation zone is further in communication with the analysis unit.

Preferably, the gas washing zone is provided with a gas washing equipment, such as a gas washing tank, wherein a gas distributor is preferably provided in the gas washing equipment for evenly distributing the incoming gas, such that the washing operation is more efficient.

According to the present disclosure, the reacted gas still has a high temperature, therefore, in order to remove the heat in a timely manner, the gas washing equipment is further provided with a cooling element, for example, a circulating water jacket provided on the outside of the gas washing equipment, for performing heat exchange to lower the temperature of the washing liquid. The heated water obtained after the heat exchange can be utilized as other heat source for sufficiently utilizing the residual heat.

According to a preferred embodiment of the present disclosure, the tail gas is subjected to washing with an alcohol, more preferably, the tail gas is subjected to a multi-stage washing with an alcohol, such as the 2-3 stages washing with an alcohol. Therefore, the gas washing zone comprises multi-stage alcohol washing tanks which are successively connected in series, in which an alcohol liquid is contained, the tail gas is in the form of bubbles by means of a gas distributor provided in the alcohol washing tank and contacts with an alcohol to carry out an alcohol washing. The alcohol may be methanol, ethanol, propanol, n-butanol, isobutanol, ethylene glycol and the like.

In accordance with a preferred embodiment of the present disclosure, the gas washing zone is in communication with the analysis unit, such that the washing process gas is subjected to the total composition detection, and the content of each ingredient in the washing process gas are determined. Accordingly, the washing process gas may be divided into at least two branches, wherein one branch is in communication with the analysis unit for performing the total component analysis, and the other branch is used for subjecting the washing process gas to a further treatment as appropriate.

According to the present disclosure, the washing process gas may be treated under the following circumstances:

Circumstance 1: if the content of the each ingredient in the washing process gas meets the expected requirements, and falls in the safe mixed gas system range without going beyond the control scope of the limit oxygen gas content, and the content of the various organic components is stable, the washing process gas can be directly used as a recycle gas and transported to the gas circulation unit.

In such a circumstance, the gas washing zone is in communication with the analysis unit and the gas circulation unit, respectively, and a valve is arranged in the communication pipeline.

Circumstance 2: if the content of an ingredient in the washing process gas is abnormal, it goes beyond the control scope of the limit oxygen gas content or the content of a combustible organic matter exceeds the explosion limit, the washing process gas is transported to a gas condensing zone for subjecting to further processing, in the meanwhile, the temperature of the gas condensing zone (i.e., the cold trap temperature) is controlled to condense the ingredients of the washing process gas respectively according to their different boiling points, such that the content reaches the safe range of the mixed gas, and the uncondensed part of the gas is then transported to the analysis unit for subjecting to component analysis. If the condition of circumstance 1 is met, the washing process gas is directly used as a recycle gas and transported to the gas circulation unit. If the condition of circumstance 1 is not met, the condensing temperature is continuously adjusted to further separate the washing process gas, such that the content reaches the safety control scope.

Thus, the gas condensing zone is preferably in communication with the analysis unit and the gas circulation unit, respectively, and a valve is arranged in the communication pipeline.

Circumstance 3: if the content of ingredients in non-condensable process gas after many times of condensation operations is still within the explosion limit scope of the combustible gas, the non-condensable process gas is transported to the gas conditioning zone for adjusting percentage of the gas; by adjusting the content percentages of ingredients in the non-condensable process gas (e.g., if the content of hydrogen gas in the non-condensable process gas is high and falls within the explosion limit scope, the propylene and oxygen gas content is increased to improve the hydrogen gas utilization rate, thereby reducing the hydrogen gas concentration at an outlet) to achieve selective consumption of reaction feed gas and thereby carrying out the securitization operation in regard to the ingredients of mixed gas entering the gas circulation unit.

Thus the gas condensing zone is preferably in communication with the analysis unit and the gas circulation unit, respectively, and a valve is arranged in the communication pipeline.

Circumstance 4: if none of the solution in circumstances 1, 2 and 3 can solve the problem of controlling the safe range of the washing process gas, the washing process gas is then transported to the tail gas discharging zone for evacuation, so as to remove it from the reaction system.

Therefore, it is preferable that a tail gas discharging zone is further provided downstream the gas conditioning zone.

According to the present disclosure, in order to accomplish circulation of the tail gas, the gas circulation unit preferably comprises a gas pressurization zone for pressurization of the recycle gas, so as to be fed to the mixing unit as at least a portion of the reaction feed gas and the diluent gas.

According to the present disclosure, it is preferable that the gas pressurization zone is provided with a low pressure gas buffer tank and a high pressure gas buffer tank which are connected in series, wherein the low pressure gas buffer tank is provided with a pressurizing device therein, and the high pressure gas buffer tank is in communication with the mixing unit. Specifically, the recycle gas is supplied to the low pressure gas buffer tank through a conduit, and when the gas pressure in the low pressure gas buffer tank reaches a threshold value, the pressurizing device is activated to pressurize the gas, and the pressurized gas is supplied to the high pressure gas buffer tank for transportation to the mixing unit as at least a portion of the reaction feed gas and the diluent gas.

Preferably, a pressure sensor is further provided in the low pressure gas buffer tank, when the gas pressure therein reaches a threshold value, the pressurizing device can be activated by the pressure sensor, for example, by opening a solenoid valve on a gas path of the pressurizing device.

Preferably, the pressurizing device is a gas booster pump.

According to the present disclosure, in order to prevent the gas from being evacuated, it is preferable that a gas return line is further provided between the high pressure gas buffer tank and the low pressure gas buffer tank to return a part of the gas in the high pressure gas buffer tank to the low pressure gas buffer tank.

Preferably, the low pressure gas buffer tank and the high pressure gas buffer tank are further independently provided with a safety valve, and the tank bottom is provided with a structure for draining liquid.

According to the present disclosure, the overall control of the reaction system is preferably implemented by a programmable logic controller (PLC), a computer can control heating, gas inlet flow, circulation gas flow and measure the data such as temperature, pressure and flow rate, and the control software has the recording and export functions. Among them, the PLC-controlled cabinet is preferably explosion-proof in design, equipped with one-key power-off button, and the PLC is provided with a computer.

According to the present disclosure, the air supply unit may comprise a hydrogen gas inlet branch, an oxygen gas inlet branch, a propylene gas inlet branch and a diluent gas inlet branch, and each of the gas inlet branches may comprise a respective gas storage tank, and a pressure reducing valve, a flow regulator and a changeable diameter joint arranged on the gas flow pipeline.

According to the present disclosure, a reactor is provided in the reaction unit, the corresponding heating and/or cooling elements and temperature control elements may be disposed in the reactor as appropriate, in order to heat and/or cool the target zone, so that the reaction temperature is controlled within the scope of the present disclosure.

According to a preferred embodiment of the present disclosure, the gases inside the reactor are heated to a predetermined reaction temperature by means of heat-conducting oil, molten salt, electric heating and the like.

According to the present disclosure, the analysis unit may be a gas chromatograph equipped with a thermal conductivity detector (TCD) and a flame ionization detector (FID).

In order to ensure accuracy of the analysis, the system preferably further comprises a heat preservation unit (e.g. a heat preservation pipeline) arranged between the reaction unit and the analysis unit and between the product separation unit and the analysis unit, so as to transport the gases to be analyzed to the analysis unit under the heat-retaining and non-condensable condition.

Accordingly, the present disclosure also provides a method for preparing epoxypropane by direct epoxidation of propylene using the system as mentioned above, the method comprises:

(1) in a mixing unit, mixing oxygen gas, optionally hydrogen gas, optionally propylene, and optionally a diluent gas in the first feed zone to obtain a first feed gas;

mixing hydrogen gas, optionally oxygen gas, optionally propylene, and optionally a diluent gas in the second feed zone to obtain a second feed gas;

wherein the materials in the first feed gas and the second feed gas are selected such that the first feed gas contains oxygen gas and is free or substantially free of hydrogen gas, the second feed gas contains hydrogen gas and is free or substantially free of oxygen gas, the first feed gas and/or the second feed gas contain propylene, at least one of the first feed gas and the second feed gas further comprises a diluent gas;

the first feed gas, the second feed gas and a recycle gas are mixed in the third feed zone to obtain a mixed gas;

(2) contacting the mixed gas with a catalyst in the reaction unit, and carrying out reaction under reaction conditions of propylene epoxidation to prepare epoxypropane;

(3) separating the products obtained from the propylene epoxidation in the product separation unit to obtain the target product epoxypropane, organic by-products and a recycle gas;

(4) subjecting the cycle gas to a pressurization treatment in the gas circulation unit, then using the cycle gas following the pressurization treatment as at least a portion of the reaction feed gas and conveying the recycle gas and the diluent gas to the mixing unit.

Preferably, the first feed gas is mixed with the second feed gas in a counter-flushing manner in the third feed zone.

Preferably, the mixed gas is preheated in the gas preheating zone.

Preferably, in the product separation unit:

(a) separating the products obtained from the propylene epoxidation in a product separation zone to obtain the target product epoxypropane, organic by-products and a recycle gas;

(b) the tail gas in a gas washing zone is subjected to washing, and the obtained washing process gas is subjected to a composition analysis, if the composition of the washing process gas is within a predetermined range, the washing process gas is used as a recycle gas and transported to the gas circulation unit; if the composition of the washing process gas is not within a predetermined range, the washing process gas is subjected to a condensation treatment;

(c) subjecting the washing process gas to at least one stage condensation in the gas condensation zone to obtain a condensate process gas and a non-condensable process gas, and the non-condensable process gas is subjected to a composition analysis; if the composition of the non-condensable process gas is within a predetermined range, the non-condensable process gas is used as a recycle gas and transported to the gas circulation unit; if the composition of the non-condensable process gas is not within a predetermined range, a gas conditioning treatment is carried out;

(d) adjusting the composition of the non-condensable process gas in the gas conditioning zone by introducing at least one of propylene, hydrogen gas, oxygen gas, and a diluent gas, and the resulting conditioned process gas is subjected to a composition analysis, and if the composition of the conditioned process gas is within a predetermined range, the conditioned process gas is used as a recycle gas and transported to the gas circulation unit; if the composition of the conditioned process gas is not within a predetermined range, the conditioned process gas is discharged outside.

The detailed description of the conditions set, catalyst selection and filling in the method for preparing epoxypropane by the epoxidation of propylene are specified in the first aspect as mentioned above, the content will not be repeatedly described herein.

The disclosure will be described in detail below with reference to examples.

As shown in FIG. 2, a reaction system for preparing epoxypropane by direct epoxidation of propylene comprises:

an air supply unit 1, comprising:

a hydrogen gas inlet branch, an oxygen gas inlet branch, a propylene gas inlet branch and a diluent gas inlet branch, each of the gas inlet branches may comprise a respective gas storage tank, and a pressure reducing valve, a flow regulator and a changeable diameter joint arranged on the gas flow pipeline;

a mixing unit 2, comprising:

a first feed zone for mixing oxygen gas, optionally hydrogen gas, optionally propylene and optionally diluent gas to obtain a first feed gas;

a second feed zone for mixing hydrogen gas, optionally oxygen gas, optionally propylene and optionally diluent gas to obtain a second feed gas;

a third feed zone for mixing the first feed gas, the second feed gas and the recycle gas to obtain a mixed gas, wherein the transfer conduit of the first feed gas is located opposite the transfer conduit of the second feed gas;

a gas preheating zone that is provided with a coiled tube type pre-heater, and its outer circumference is provided with heat-conductive oil for preheating the mixed gas;

a reaction unit 3, comprising:

a reaction zone that is provided with a tubular reactor (made of stainless steel, and has a volume of 316L), its outer circumference is provided with heat-conductive oil for heating, the preheated mixed gas carries out reaction in the reaction zone, wherein the length of the tubular reactor is 3 m, and the catalyst is filled in the tubular reactor, and the reaction products outlet of the tubular reactor is in communication with the analysis unit 6 through a pipeline to facilitate the composition analysis of the reaction products;

a product separation unit 4, comprising:

a product separation zone, a gas washing zone, a gas condensing zone, a gas conditioning zone and a tail gas discharging zone sequentially connected in series, wherein the gas washing zone, the gas condensing zone and the gas conditioning zone are each provided with a pipeline in communication with the gas circulation unit 5 and the analysis unit 6, respectively, and the pipeline is provided with a valve.

The product separation zone is used for separating products from the propylene epoxidation to obtain the target product epoxypropane, organic by-products and a tail gas; a back pressure valve is disposed at an outlet of the product separation zone, a portion of the tail gas is introduced into the analysis unit 6 through a heat preservation pipeline (150° C.) for performing a whole composition analysis and the remaining tail gas is introduced into the gas washing zone; wherein the gas washing zone comprises two-stage alcohol washing tanks, a gas distributor is provided in an inlet pipeline of each stage of the alcohol washing tank, the tail gas is in the form of bubbles by means of a gas distributor to carry out an alcohol washing, a circulation water jacket is arranged outside the alcohol washing tank for lowering the temperature of the alcohol washing liquid. A portion of the washing process gas is introduced into the analysis unit 6 through a four-way valve for subjecting to a whole composition analysis;

Circumstance 1: if the content of the each ingredient in the washing process gas meets the expected requirements, and falls in the safe mixed gas system range without going beyond the control scope of the limit oxygen gas content, and the content of the various organic components is stable, the washing process gas can be directly introduced into the gas circulation unit.

Circumstance 2: if the content of an ingredient in the washing process gas is abnormal, it goes beyond the control scope of limit oxygen gas content or the content of a combustible organic matter exceeds the explosive limit, the washing process gas is transported to the gas condensing zone for subjecting to the further processing, in the meanwhile, the temperature of the gas condensing zone (i.e., the cold trap temperature) is controlled to condense the ingredients of the washing process gas respectively according to their different boiling points, such that the content reaches the safe range of the mixed gas, and the uncondensed part of the gas is then transported to the analysis unit 6 for component analysis. If the condition of circumstance 1 is met, the washing process gas is subjected to the subsequent circulation treatment. If the condition of circumstance 1 is not met, the condensing temperature is continuously adjusted to further separate the washing process gas, such that the content reaches the safety control scope of the mixture concentration.

Circumstance 3: if the content of ingredient in the obtained mixture introduced into the analysis unit 6 after many times of condensation operations is still within the explosion limit scope of the combustible gas, the content percentages of raw materials in the gas conditioning zone is adjusted (e.g., if the content of hydrogen gas in the mixture is high and falls within the explosion limit scope, the propylene and oxygen gas content is increased to improve the hydrogen gas utilization rate, thereby reducing the hydrogen gas concentration at an outlet) to achieve selective consumption of reaction feed gas and thereby carrying out the securitization operation in regard to the ingredients of mixed gas entering the gas circulation unit.

Circumstance 4: if none of the solution in circumstances 1, 2 and 3 can solve the problem of controlling the safe range of the mixed gas, the mixed gas is then transported to the tail gas discharging zone for evacuation, so as to remove it from the reaction system.

A gas circulation unit 5, comprises:

a gas pressurization zone, which includes a low pressure gas buffer tank and a high pressure gas buffer tank; the recycle gas is divided into two routes, one route of the recycle gas is vented through a rotameter, and the other route of the recycle gas is introduced into the low pressure gas buffer tank. When the pressure of the gas buffer tank is depressed to reach the threshold value, the solenoid valve for opening the gas path of the pressurizing device (gas booster pump) is activated by means of the pressure sensor, so that the pressurizing device starts to operate, the pressurized gas enters the high pressure gas buffer tank, a part of the gas in the high pressure buffer tank passes through a mass flow meter and enters the gas mixing zone, so that the gas pressurizing cycle is performed; another part of the gas is returned to the low pressure gas buffer tank of the preceding stage through the back pressure valve, so that the gas is prevented from being evacuated, the high pressure buffer tank is provided with a safety valve, and the tank bottom is provided with a structure for draining liquid.

The overall control of the reaction system is preferably implemented by a programmable logic controller (PLC), a computer can control heating, gas inlet flow, circulation gas flow and measure the data such as temperature, pressure and flow rate, and the control software has the recording and export functions; the PLC-controlled cabinet is explosion-proof in design, equipped with one-key power-off button, and the device is provided with a computer.

An analysis unit 6, comprises:

two gas chromatographs which were used for collecting sample of the products and carrying out the gas chromatographic analysis. Both of the gas chromatographs were Agilent 7890B, wherein the chromatography column of the gas chromatograph A was (1) HayeSep Q column (SFt 0.9 m, OD ⅛, ID 2 mm), (2) Molsieve 5 A column (SFt 2.44 m, OD ⅛, ID 2 mm), (3) PoraBOND U column (25 m, 0.32 mm, 7 μm), it was equipped with TCD and FID detectors for analyzing permanent gases such as $H_2$, $O_2$, diluent gas, and propylene, propane, epoxypropane, acrolein, acetone, propylaldehyde, acetaldehyde and the like, wherein the peak positions of the propylene and hydrogen gas are similar and their mutual influence cannot be accurately distinguished, thus the gas chromatograph B was used to assist the analysis. The chromatography column of the gas chromatograph B was (1) HayeSep Q column (SFt 1.83 m, OD ⅛, ID 2 mm), (2) Molsieve 5 A column (SFt 2.44 m, OD ⅛, ID 2 mm), (3) HP-AL\S column (25 m, 0.32 mm, 8 μm), it was equipped with TCD and FID detectors for analyzing permanent gases such as $H_2$, $O_2$, diluent gas, and propylene and propane.

In the Au@TS-1 molecular sieve catalyst, the TS-1 molecular sieve was prepared by means of hydro-thermal synthesis, and the active metal Au was supported by means of deposition-precipitation.

Embodiment I

Combustion and Explosion Test

In the aforementioned reaction system, 30 g of Au@TS-1 molecular sieve catalyst (the loading amount of Au was 1 wt %) and 1,200 g of quartz sand were filled in the reactor in a layered stacking manner with respect to 1,000 mL of reactor, as shown in FIG. 1C, wherein the layer height ratio of the catalyst layer and the quartz sand layer was 1:2, the catalyst layer and the inert filler layer were each independently 15 layers/m, and a direct epoxidation with gas phase propylene was carried out according to the following mode:

(1) the diluent gas, propylene and oxygen gas were mixed in a ratio of 1:1:1 to obtain a first feed gas, the oxygen gas concentration was in compliance with the formula (1);

(2) the first feed gas was mixed with hydrogen gas applied as the second feed gas in a counter-flushing manner with an angle of 180° to obtain a mixed gas, wherein the ratio of hydrogen gas, oxygen gas, propylene and diluent gas was 1:1:1:1, the oxygen gas concentration was in compliance with the formula (1);

(3) the mixed gas was introduced into the gas preheating zone, preheated to 160° C. and subsequently entered the reaction unit for carrying out reaction, the volumetric hourly space velocity of the reaction was 4,000 mL $g_{cat}^{-1}$ $h^{-1}$, the reaction pressure of the system was controlled to be 0.2 MPa, and temperature was raised to 200° C. at a programmed temperature rise rate of 1.5° C. $min^{-1}$.

In the case of that the diluent gas was nitrogen gas, the reaction system did not explode during the reaction time of 20 min.

The system cannot be safely operated without adopting the aforementioned mode of introducing gas in a step-by-step manner.

In the case that the diluent gas was propylene, propane and methane, the reaction system did not explode during the reaction time of 20 min.

As can be seen, the method of the present disclosure can also guarantee safety of the reaction under a circumstance of reducing the used amount of diluent gas.

Example 1

The example served to illustrate a method for direct epoxidation of propylene provided by the present disclosure.

In the aforementioned reaction system, 30 g of Au@TS-1 molecular sieve catalyst (the loading amount of Au was 1 wt %) and 1,200 g of quartz sand were filled in the reactor in a layered stacking manner with respect to 1,000 mL of reactor, as shown in FIG. 1C, wherein the layer height ratio of the catalyst layer and the quartz sand layer was 1:1.5, the catalyst layer and the inert filler layer were each independently 10 layers/m, and the direct epoxidation with gas phase propylene was carried out according to the following mode:

The mixing was carried out according to gas mixing mode in the "Combustion and Explosion test", the diluent gas was nitrogen gas, the mixed gas was then introduced into the gas preheating zone, preheated to 160° C. and subsequently entered the reaction unit for carrying out reaction, the volumetric hourly space velocity of the reaction was 4,000 mL $g_{cat}^{-1}$ $h^{-1}$, the reaction pressure of the system was controlled to be 0.15 MPa, and temperature was raised to 200° C. at a programmed temperature rise rate of 1.5° C. $min^{-1}$.

The product obtained after the reaction was treated by the product separation unit and the gas circulation unit, and introduced into the mixed gas for recycling.

After the reaction was stabilized, an analysis on the direct epoxidation of gas phase propylene was carried out, the analysis results were shown in Table 1, and an approximate time when the indicators such as propylene conversion rate and epoxypropane selectivity started to decline was recorded (the recording was performed once for every 50 hours).

Example 2

The example served to illustrate a method for direct epoxidation of propylene provided by the present disclosure.

In the aforementioned reaction system, 30 g of Au@TS-1 molecular sieve catalyst (the loading amount of Au was 1 wt %) and 900 g of quartz sand were filled in the reactor in a layered stacking manner with respect to 1,000 mL of reactor, as shown in FIG. 1C, wherein the layer height ratio of the catalyst layer and the quartz sand layer was 1:2.5, the catalyst layer and the inert filler layer were each independently 20 layers/m, and the direct epoxidation with gas phase propylene was carried out according to the following mode:

The mixing was carried out according to gas mixing mode in the "Combustion and Explosion test", the diluent gas was nitrogen gas, the mixed gas was then introduced into the gas preheating zone, preheated to 130° C. and subsequently entered the reaction unit for carrying out reaction, the volumetric hourly space velocity of the reaction was 9,000 mL $g_{cat}^{-1}$ $h^{-1}$, the reaction pressure of the system was controlled to be 0.05 MPa, and temperature was raised to 170° C. at a programmed temperature rise rate of 1.2° C. $min^{-1}$.

The product obtained after the reaction was treated by the product separation unit and the gas circulation unit, and introduced into the mixed gas for recycling.

After the reaction was stabilized, an analysis on the direct epoxidation of gas phase propylene was carried out, the analysis results were shown in Table 1, and an approximate time when the indicators such as propylene conversion rate and epoxypropane selectivity started to decline was recorded (the recording was performed once for every 50 hours).

Example 3

The example served to illustrate a method for direct epoxidation of propylene provided by the present disclosure.

In the aforementioned reaction system, 30 g of Au@TS-1 molecular sieve catalyst (the loading amount of Au was 1 wt %) and 1,350 g of quartz sand were filled in the reactor in a layered stacking manner with respect to 1,000 mL of reactor, as shown in FIG. 1C, wherein the layer height ratio of the catalyst layer and the quartz sand layer was 1:2, the catalyst layer and the inert filler layer were each independently 15 layers/m, and the direct epoxidation with gas phase propylene was carried out according to the following mode:

the mixing was carried out according to gas mixing mode in the "Combustion and Explosion test", the diluent gas was nitrogen gas, the mixed gas was then introduced into the gas preheating zone, preheated to 100° C. and subsequently entered the reaction unit for carrying out reaction, the volumetric hourly space velocity of the reaction was 15,000 mL $g_{cat}^{-1}$ $h^{-1}$, the reaction pressure of the system was controlled to be 0.25 MPa, and temperature was raised to 120° C. at a programmed temperature rise rate of 1.5° C. $min^{-1}$.

The product obtained after the reaction was treated by the product separation unit and the gas circulation unit, and introduced into the mixed gas for recycling.

After the reaction was stabilized, an analysis on the direct epoxidation of gas phase propylene was carried out, the analysis results were shown in Table 1, and an approximate time when the indicators such as propylene conversion rate and epoxypropane selectivity started to decline was recorded (the recording was performed once for every 50 hours).

Example 4

The example served to illustrate a method for direct epoxidation of propylene provided by the present disclosure.

In the aforementioned reaction system, 30 g of Au@TS-1 molecular sieve catalyst (the loading amount of Au was 1 wt %) and 500 g of quartz sand were filled in the reactor in a layered stacking manner with respect to 1,000 mL of reactor, as shown in FIG. 1C, wherein the layer height ratio of the catalyst layer and the quartz sand layer was 1:1.2, the catalyst layer and the inert filler layer were each independently 8 layers/m, and the direct epoxidation with gas phase propylene was carried out according to the following mode:

The mixing was carried out according to gas mixing mode in the "Combustion and Explosion test", the diluent gas was nitrogen gas, the mixed gas was then introduced into the gas preheating zone, preheated to 80° C. and subsequently entered the reaction unit for carrying out reaction, the volumetric hourly space velocity of the reaction was 20,000 mL $g_{cat}^{-1}$ $h^{-1}$, the reaction pressure of the system was controlled to be 0.5 MPa, and temperature was raised to 110° C. at a programmed temperature rise rate of 0.3° C. $min^{-1}$.

The product obtained after the reaction was treated by the product separation unit and the gas circulation unit, and introduced into the mixed gas for recycling.

After the reaction was stabilized, an analysis on the direct epoxidation of gas phase propylene was carried out, the analysis results were shown in Table 1, and an approximate time when the indicators such as propylene conversion rate and epoxypropane selectivity started to decline was recorded (the recording was performed once for every 50 hours).

Example 5

The example served to illustrate a method for direct epoxidation of propylene provided by the present disclosure In the aforementioned reaction system, 30 g of Au@TS-1 molecular sieve catalyst (the loading amount of Au was 1 wt %) and 1,500 g of quartz sand were filled in the reactor in a layered stacking manner with respect to 1,000 mL of reactor, as shown in FIG. 1C, wherein the layer height ratio of the catalyst layer and the quartz sand layer was 1:4, the catalyst layer and the inert filler layer were each independently 15 layers/m, and the direct epoxidation with gas phase propylene was carried out according to the following mode:

The mixing was carried out according to gas mixing mode in the "Combustion and Explosion test", the diluent gas was nitrogen gas, the mixed gas was then introduced into the gas preheating zone, preheated to 100° C. and subsequently entered the reaction unit for carrying out reaction, the volumetric hourly space velocity of the reaction was 1,000 mL $g_{cat}^{-1}$ $h^{-1}$, the reaction pressure of the system was controlled to be 0.02 MPa, and temperature was raised to 230° C. at a programmed temperature rise rate of 5° C. $min^{-1}$.

The product obtained after the reaction was treated by the product separation unit and the gas circulation unit, and introduced into the mixed gas for recycling.

After the reaction was stabilized, an analysis on the direct epoxidation of gas phase propylene was carried out, the analysis results were shown in Table 1, and an approximate time when the indicators such as propylene conversion rate and epoxypropane selectivity started to decline was recorded (the recording was performed once for every 50 hours).

Example 6

The example served to illustrate a method for direct epoxidation of propylene provided by the present disclosure.

The epoxypropane was prepared through direct epoxidation of propylene according to the method of Example 2, except that the catalyst was filled in a mode as shown in FIG. 1B. The analysis results were shown in Table 1.

Example 7

The example served to illustrate a method for direct epoxidation of propylene provided by the present disclosure.

The epoxypropane was prepared through direct epoxidation of propylene according to the method of Example 2, except that the catalyst was filled in a mode as shown in FIG. 1A. The analysis results were shown in Table 1.

Example 8

The example served to illustrate a method for direct epoxidation of propylene provided by the present disclosure.

The epoxypropane was prepared through direct epoxidation of propylene according to the method of Example 2, except that the preheating was not carried out prior to the mixed gas entered the reaction unit. The analysis results were shown in Table 1.

Example 9

The example served to illustrate a method for direct epoxidation of propylene provided by the present disclosure.

The epoxypropane was prepared through direct epoxidation of propylene according to the method of Example 2, except that the diluent gas was propylene.

Example 10

The example served to illustrate a method for direct epoxidation of propylene provided by the present disclosure.

The epoxypropane was prepared through direct epoxidation of propylene according to the method of Example 2, except that the diluent gas was methane.

Example 11

The example served to illustrate a method for direct epoxidation of propylene provided by the present disclosure.

The epoxypropane was prepared through direct epoxidation of propylene according to the method of Example 2, except that the diluent gas was propane.

Example 12

The example served to illustrate a method for direct epoxidation of propylene provided by the present disclosure.

The epoxypropane was prepared through direct epoxidation of propylene according to the method of Example 1, except that the gas obtained after the reaction was not subjected to circulation.

Comparative Example 1

The comparative example served to illustrate a method for direct epoxidation of propylene as a reference.

The epoxypropane was prepared through direct epoxidation of propylene according to the method of Example 12, except that the mixing of gases was not carried out in a step-by-step manner, but directly mixing the gases; in order to ensure smooth progress of the reaction, the ratio of $H_2$:$O_2$:$C_3H_6$:$N_2$=1:1:1:7 was obtained through adjustment. The analysis results were shown in Table 1.

TABLE 1

| | Propylene conversion rate (%) | Epoxypropane selectivity (%) | Hydrogen gas utilization (%) | Service life of catalyst (h) | Space-time yield ($g_{PO}$ $kg_{cat}^{-1}$ $h^{-1}$) |
|---|---|---|---|---|---|
| Example 1 | 21.8 | 84.0 | 24.5 | 850 | 216.3 |
| Example 2 | 19.2 | 85.5 | 27.6 | 1000 | 957.5 |
| Example 3 | 17.8 | 83.2 | 24.0 | 1500 | 1205.6 |
| Example 4 | 9.6 | 76.5 | 17.8 | 1200 | 1957.8 |
| Example 5 | 17.0 | 70.6 | 11.8 | 500 | 93.9 |
| Example 6 | 14.2 | 82.5 | 23.2 | 750 | 716.8 |
| Example 7 | 14.0 | 78.9 | 21.3 | 700 | 757.9 |
| Example 8 | 10.7 | 79.5 | 21.2 | 550 | 586.5 |
| Example 9 | 22.9 | 86.5 | 28.6 | 1000 | 1685.2 |
| Example 10 | 21.5 | 85.7 | 27.0 | 850 | 952.6 |
| Example 11 | 21.0 | 86.1 | 27.2 | 950 | 1010.6 |
| Example 12 | 6.2 | 84.1 | 24.8 | 750 | 274.5 |
| Comparative Example 1 | 4.3 | 73.0 | 15.5 | 100 | 128.9 |

Note:
the conversion rate of propylene in Example 9 was calculated only for the propylene used as a reactant gas, and the amount of propylene as a diluent gas was not included, i.e., when the conversion rate of propylene was calculated by analyzing the amounts of ingredients in the gas obtained after the reaction, the amount of propylene used as a diluent gas shall be subtracted therefrom, it was considered that the diluent gas did not participate the reaction.

Embodiment II

Combustion and Explosion Test

In a tubular reactor, 30 g of Au@TS-1 molecular sieve catalyst (the loading amount of Au was 1 wt %) and 1,200 g of quartz sand were filled in the reactor in a layered stacking manner with respect to 1,000 mL of reactor, as shown in FIG. 1C, wherein the layer height ratio of the catalyst layer and the quartz sand layer was 1:2, the catalyst layer and the inert filler layer were each independently 15 layers/m, and a direct epoxidation with gas phase propylene was carried out according to the following mode of introducing gas:

(1) the diluent gas, propylene and hydrogen gas were mixed in a ratio of 1:1:1 to obtain a second feed gas;
(2) the second feed gas was mixed with oxygen gas applied as the first feed gas in a counter-flushing manner with an angle of 180° to obtain a mixed gas, wherein a ratio of hydrogen gas, oxygen gas, propylene and the diluent gas was 1:1:1:1;

(3) the mixed gas was introduced into the gas preheating zone, preheated to 160° C. and subsequently entered the reaction unit for carrying out reaction, the volumetric hourly space velocity of the reaction was 4,000 mL $g_{cat}^{-1}$ $h^{-1}$, the reaction pressure of the system was controlled to be 0.2 MPa, and temperature was raised to 200° C. through a program that each temperature rise of 5° C. was followed by the heat preservation for 5 min.

In the case of that the diluent gas was water vapor, the reaction system did not explode during the reaction time of 20 min.

The system cannot be safely operated without adopting the aforementioned mode of introducing gas in a step-by-step manner.

In the case that the diluent gas was carbon monoxide and nitrogen gas, the reaction system did not explode during the reaction time of 20 min.

As can be seen, the method of the present disclosure can also guarantee safety of the reaction under a circumstance of reducing the used amount of the diluent gas.

Example 1

The example served to illustrate a method for direct epoxidation of propylene provided by the present disclosure.

In the tubular reaction system, 30 g of Au@TS-1 molecular sieve catalyst (the loading amount of Au was 1 wt %) and 1,200 g of quartz sand were filled in a reactor in a layered stacking manner with respect to 1,000 mL of the reactor, as shown in FIG. 1C, wherein the layer height ratio of the catalyst layer and the quartz sand layer was 1:2, the catalyst layer and the inert filler layer were each independently 15 layers/m, and the direct epoxidation with gas phase propylene was carried out according to the following mode:

The mixing was carried out according to the second gas mixing mode (the gas mixing mode in "Combustion and Explosion test" of Embodiment II), the diluent gas was water vapor, the third mixed gas (the mixed gas in step (2) of introducing gas in "Combustion and Explosion test" of Embodiment II) was then introduced into the gas preheating zone, preheated to 160° C. and subsequently entered the reaction unit for carrying out reaction, the volumetric hourly space velocity of the reaction was 9,000 mL $g_{cat}^{-1}$ $h^{-1}$, the reaction pressure of the system was controlled to be 0.15 MPa, and temperature was raised to 200° C. at a program that each temperature rise of 5° C. was followed by the heat preservation for 10 min.

The product obtained after the reaction was subjected to a product separation to obtain the target product, organic by-products, and a tail gas which was not completely reacted, the tail gas was treated and introduced into the third mixed gas for recycling.

After the reaction was stabilized, an analysis on the direct epoxidation of gas phase propylene was carried out, the analysis results were shown in Table 2, and an approximate time when the indicators such as propylene conversion rate and epoxypropane selectivity started to decline was recorded (the recording was performed once for every 50 hours).

Example 2

The example served to illustrate a method for direct epoxidation of propylene provided by the present disclosure.

In the tubular reaction system, 30 g of Au@TS-1 molecular sieve catalyst (the loading amount of Au was 1 wt %) and 900 g of quartz sand were filled in a reactor in a layered stacking manner with respect to 1,000 mL of the reactor, as shown in FIG. 1C, wherein the layer height ratio of the catalyst layer and the quartz sand layer was 1:1.5, the catalyst layer and the inert filler layer were each independently 10 layers/m, and the direct epoxidation with gas phase propylene was carried out according to the following mode:

The mixing was carried out according to the second gas mixing mode in the "Combustion and Explosion test" of Embodiment II, the diluent gas was water vapor, the third mixed gas was then introduced into the gas preheating zone, preheated to 130° C. and subsequently entered the reaction unit for carrying out reaction, the volumetric hourly space velocity of the reaction was 15,000 mL $g_{cat}^{-1}$ $h^{-1}$, the reaction pressure of the system was controlled to be 0.05 MPa, and temperature was raised to 170° C. at a program that each temperature rise of 8° C. was followed by the heat preservation for 8 min.

The product obtained after the reaction was subjected to a product separation to obtain the target product, organic by-products, and a tail gas which was not completely reacted, the tail gas was treated and introduced into the third mixed gas for recycling.

After the reaction was stabilized, an analysis on the direct epoxidation of gas phase propylene was carried out, the analysis results were shown in Table 2, and an approximate time when the indicators such as propylene conversion rate and epoxypropane selectivity started to decline was recorded (the recording was performed once for every 50 hours).

Example 3

The example served to illustrate a method for direct epoxidation of propylene provided by the present disclosure.

In the tubular reaction system, 30 g of Au@TS-1 molecular sieve catalyst (the loading amount of Au was 1 wt %) and 1,350 g of quartz sand were filled in a reactor in a layered stacking manner with respect to 1,000 mL of the reactor, as shown in FIG. 1C, wherein the layer height ratio of the catalyst layer and the quartz sand layer was 1:2.5, the catalyst layer and the inert filler layer were each independently 20 layers/m, and the direct epoxidation with gas phase propylene was carried out according to the following mode:

The mixing was carried out according to the second gas mixing mode in the "Combustion and Explosion test" of Embodiment II, the diluent gas was water vapor, the third mixed gas was then introduced into the gas preheating zone, preheated to 100° C. and subsequently entered the reaction unit for carrying out reaction, the volumetric hourly space velocity of the reaction was 4,000 mL $g_{cat}^{-1}$ $h^{-1}$, the reaction pressure of the system was controlled to be 0.25 MPa, and temperature was raised to 120° C. at a program that each temperature rise of 10° C. was followed by the heat preservation for 5 min.

The product obtained after the reaction was subjected to a product separation to obtain the target product, organic by-products, and a tail gas which was not completely reacted, the tail gas was treated and introduced into the third mixed gas for recycling.

After the reaction was stabilized, an analysis on the direct epoxidation with gas phase propylene was carried out, the analysis results were shown in Table 2, and an approximate time when the indicators such as propylene conversion rate and epoxypropane selectivity started to decline was recorded (the recording was performed once for every 50 hours).

Example 4

The example served to illustrate a method for direct epoxidation of propylene provided by the present disclosure.

In the tubular reaction system, 30 g of Au@TS-1 molecular sieve catalyst (the loading amount of Au was 1 wt %) and 500 g of quartz sand were filled in a reactor in a layered stacking manner with respect to 1,000 mL of the reactor, as shown in FIG. 1C, wherein the layer height ratio of the catalyst layer and the quartz sand layer was 1:1, the catalyst layer and the inert filler layer were each independently 15 layers/m, and the direct epoxidation with gas phase propylene was carried out according to the following mode:

The mixing was carried out according to the second gas mixing mode in the "Combustion and Explosion test" of Embodiment II, the diluent gas was water vapor, the third mixed gas was then introduced into the gas preheating zone, preheated to 100° C. and subsequently entered the reaction unit for carrying out reaction, the volumetric hourly space velocity of the reaction was 1,000 mL $g_{cat}^{-1}$ $h^{-1}$, the reaction pressure of the system was controlled to be 0.5 MPa, and temperature was raised to 100° C. at a program that each temperature rise of 2° C. was followed by the heat preservation for 1 min.

The product obtained after the reaction was subjected to a product separation to obtain the target product, organic by-products, and a tail gas which was not completely reacted, the tail gas was treated and introduced into the third mixed gas for recycling.

After the reaction was stabilized, an analysis on the direct epoxidation of gas phase propylene was carried out, the analysis results were shown in Table 2, and an approximate time when the indicators such as propylene conversion rate and epoxypropane selectivity started to decline was recorded (the recording was performed once for every 50 hours).

Example 5

The example served to illustrate a method for direct epoxidation of propylene provided by the present disclosure.

In the tubular reaction system, 30 g of Au@TS-1 molecular sieve catalyst (the loading amount of Au was 1 wt %) and 1,500 g of quartz sand were filled in a reactor in a layered stacking manner with respect to 1,000 mL of the reactor, as shown in FIG. 1C, wherein the layer height ratio of the catalyst layer and the quartz sand layer was 1:3, the catalyst layer and the inert filler layer were each independently 15 layers/m, and the direct epoxidation with gas phase propylene was carried out according to the following mode:

The mixing was carried out according to the second gas mixing mode in the "Combustion and Explosion test" of Embodiment II, the diluent gas was water vapor, the third mixed gas was then introduced into the gas preheating zone, preheated to 100° C. and subsequently entered the reaction unit for carrying out reaction, the volumetric hourly space velocity of the reaction was 20,000 mL $g_{cat}^{-1}$ $h^{-1}$, the reaction pressure of the system was controlled to be 0.01 MPa, and temperature was raised to 250° C. at a program that each temperature rise of 15° C. was followed by the heat preservation for 10 min.

The product obtained after the reaction was subjected to a product separation to obtain the target product, organic by-products, and a tail gas which was not completely reacted, the tail gas was treated and introduced into the third mixed gas for recycling.

After the reaction was stabilized, an analysis on the direct epoxidation of gas phase propylene was carried out, the analysis results were shown in Table 2, and an approximate time when the indicators such as propylene conversion rate and epoxypropane selectivity started to decline was recorded (the recording was performed once for every 50 hours).

Example 6

The example served to illustrate a method for direct epoxidation of propylene provided by the present disclosure.

The epoxypropane was prepared through direct epoxidation of propylene according to the method of Example 1, except that the catalyst was filled in a mode as shown in FIG. 1B. The analysis results were shown in Table 2.

Example 7

The example served to illustrate a method for direct epoxidation of propylene provided by the present disclosure.

The epoxypropane was prepared through direct epoxidation of propylene according to the method of Example 1, except that the catalyst was filled in a mode as shown in FIG. 1A. The analysis results were shown in Table 2.

Example 8

The example served to illustrate a method for direct epoxidation of propylene provided by the present disclosure.

The epoxypropane was prepared through direct epoxidation of propylene according to the method of Example 1, except that the preheating was not carried out prior to the mixed gas entered the reaction unit. The analysis results were shown in Table 2.

Example 9

The example served to illustrate a method for direct epoxidation of propylene provided by the present disclosure.

The epoxypropane was prepared through direct epoxidation of propylene according to the method of Example 1, except that the gas obtained after the reaction was not subjected to circulation. The analysis results were shown in Table 2.

Example 10

The example served to illustrate a method for direct epoxidation of propylene provided by the present disclosure.

The epoxypropane was prepared through direct epoxidation of propylene according to the method of Example 1, except that the diluent gas was nitrogen gas. The analysis results were shown in Table 2.

Example 11

The example served to illustrate a method for direct epoxidation of propylene provided by the present disclosure.

The epoxypropane was prepared through direct epoxidation of propylene according to the method of Example 1, except that the diluent gas was carbon monoxide. The analysis results were shown in Table 2.

Comparative Example 1

The comparative example served to illustrate a method for direct epoxidation of propylene as a reference.

The epoxypropane was prepared through direct epoxidation of propylene according to the method of Example 9, except that the mixing of gases was not carried out in a step-by-step manner, but directly mixing the gases, the diluent gas was nitrogen gas; in order to ensure smooth progress of the reaction, the ratio of $H_2:O_2:C_3H_6:N_2=1:1:1:7$ was obtained through adjustment. The analysis results were shown in Table 2.

TABLE 2

| | Propylene conversion rate (%) | Epoxypropane selectivity (%) | Hydrogen gas utilization (%) | Service life of catalyst (h) | Space-time yield ($g_{PO}$ $kg_{cat}^{-1}$ $h^{-1}$) |
|---|---|---|---|---|---|
| Example 1 | 22.1 | 84.5 | 25.1 | 850 | 956.4 |
| Example 2 | 19.8 | 86.1 | 27.7 | 900 | 1208.3 |
| Example 3 | 17.7 | 83.5 | 24.0 | 1550 | 216.7 |
| Example 4 | 9.9 | 76.4 | 17.9 | 1150 | 94.2 |
| Example 5 | 17.2 | 70.6 | 11.8 | 600 | 1966.8 |
| Example 6 | 14.6 | 83.0 | 23.5 | 750 | 718.9 |
| Example 7 | 14.4 | 78.9 | 20.8 | 650 | 758.3 |
| Example 8 | 11.1 | 79.5 | 21.3 | 600 | 587.0 |
| Example 9 | 6.5 | 84.1 | 25.0 | 800 | 275.3 |
| Example 10 | 21.5 | 84.5 | 25.1 | 850 | 1682.7 |
| Example 11 | 21.7 | 85.7 | 27.2 | 900 | 953.5 |
| Comparative Example 1 | 4.1 | 73.0 | 15.2 | 100 | 129.9 |

As shown in Table 1 and Table 2, the present disclosure can effectively reduce the used amount of the catalyst (under the normal conditions, the used amount of the catalyst shall be at least 100 g relative to a 1,000 ml reactor), and significantly lower dosage of the diluent gas, as a result, the concentration of reactant is significantly improved and the energy consumption is greatly decreased. At the same time, there is a significant improvement in the propylene conversion rate, epoxypropane selectivity and the hydrogen gas utilization. As can be seen, the technical solution of the present disclosure can produce better effects with the same catalyst dosage, thus the present disclosure can lower the catalyst dosage.

By using the tubular reactor of the present disclosure, the direct epoxidation process of gas phase propylene can be stably operated for at least 500 hours, if the process is combined with the more preferred conditions of the present disclosure, e.g., specific reaction conditions, specific mode of filling the catalyst, the process can be stably operated for 1,000 hours or more.

In addition, by recycling of the gas, the technical solution of the present disclosure can increase conversion rate of the propylene without comprising the service life of the catalyst, thereby achieving the full utilization of the raw materials.

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

The invention claimed is:

1. A method for preparing epoxypropane by direct epoxidation of propylene comprising:

mixing a first feed gas and a second feed gas to form a mixed gas; and contacting the mixed gas with a catalyst under reaction conditions that cause propylene epoxidation to produce epoxypropane, wherein the first feed gas contains oxygen gas and is free or substantially free of hydrogen gas, the second feed gas contains hydrogen gas and is free or substantially free of oxygen gas, the first feed gas and/or the second feed gas contain propylene, at least one of the first feed gas and the second feed gas further comprises a diluent gas, and wherein the mixed gas contains up to 70 vol % of the diluent gas and at least 20 vol % of oxygen, and wherein the propylene epoxidation is performed in the absence of a solvent.

2. The method of claim 1, wherein the diluent gas is an inert diluent gas, a non-inert diluent gas, or a mixture thereof.

3. The method of claim 2, wherein the inert diluent gas is selected from the group consisting of $N_2$, Ar and $CO_2$; and/or the non-inert diluent gas is a gaseous alkane.

4. The method of claim 3, wherein the gaseous alkane is a $C_1$-$C_4$ alkane.

5. The method of claim 1, wherein, the first feed gas contains oxygen gas and is free or substantially free of hydrogen gas, containing at least a portion of propylene and at least a portion of diluent gas, and the second feed gas contains hydrogen gas and is free or substantially free of oxygen gas, containing the remainder of propylene and the remainder of the diluent gas; or the second feed gas contains hydrogen gas and is free or substantially free of oxygen gas, containing at least a portion of propylene and at least a portion of diluent gas, and the first feed gas contains oxygen gas and is free or substantially free of hydrogen gas, containing the remainder of propylene and the remainder of the diluent gas.

6. The method of claim 1, wherein the second feed gas is mixed with the first feed gas in a counter-flushing manner.

7. The method of claim 1, further comprising a step of preheating the mixed gas prior to contacting the mixed gas with the catalyst.

8. The method of claim 1, wherein the catalyst is a supported metal catalyst comprising a carrier and an active metal component, the active metal component is at least one selected from the group consisting of gold, silver, copper, ruthenium, palladium, platinum, rhodium, cobalt, nickel, tungsten, bismuth, molybdenum and oxides thereof, the carrier is at least one selected from the group consisting of carbon black, activated carbon, silica, alumina, ceria and zeolite, the content of the active metal component in terms of the metal element in the catalyst is 0.01-50 wt %, based on the total weight of the catalyst.

9. The method of claim 1, wherein the catalyst is filled in the reactor in combination of an inert filler;

the inert filler is at least one selected from the group consisting of silica sand, $Al_2O_3$, porous silica gel and ceramic ring;

the inert filler is used in an amount of 1-200 parts by weight with respect to 1 part by weight of the catalyst; and the catalyst and the inert filler are filled in the reactor in a layered stacking manner.

10. The method of claim 1, wherein the reaction conditions that cause propylene epoxidation comprise: a reaction temperature of 20-300° C.; a reaction pressure of 0-5 MPa; and a volumetric hourly space velocity of the mixed gas of 500-30,000 mL $g_{cat}^{-1}$ $h^{-1}$.

11. The method of claim 1, further comprising: separating products from the propylene epoxidation to obtain the target product epoxypropane, organic by-products and a recycle gas, and introducing the recycle gas into the mixed gas.

12. The method of claim 8, wherein the carrier is a titanium-silicon molecular sieve and the active metal component is gold.

13. The method of claim 9, wherein the catalyst and the inert filler are filled in the reactor in alternating layers, and a height ratio of a layer of the catalyst to a layer of the inert filler is 1:1-10.

14. The method of claim 10, wherein the reaction conditions of propylene epoxidation comprise: a reaction temperature of 50-250° C.; a reaction pressure of 0-1.5 MPa; and a volumetric hourly space velocity of the mixed gas of 1,000-20,000 mL $g_{cat}^{-1}$ $h^{-1}$.

* * * * *